US006919036B2

(12) United States Patent
Schubert

(10) Patent No.: US 6,919,036 B2
(45) Date of Patent: Jul. 19, 2005

(54) NONABORATE COMPOSITIONS AND THEIR PREPARATION

(75) Inventor: David M. Schubert, Los Angeles, CA (US)

(73) Assignee: U.S. Borax Inc., Valencia, CA (US)

( * ) Notice: Subject to any disclaimer, the term of this patent is extended or adjusted under 35 U.S.C. 154(b) by 425 days.

(21) Appl. No.: 10/181,628

(22) PCT Filed: Jan. 18, 2001

(86) PCT No.: PCT/US01/01711

§ 371 (c)(1),
(2), (4) Date: Jul. 19, 2002

(87) PCT Pub. No.: WO01/53201

PCT Pub. Date: Jul. 26, 2001

(65) Prior Publication Data

US 2003/0109751 A1 Jun. 12, 2003

Related U.S. Application Data

(60) Provisional application No. 60/177,467, filed on Jan. 21, 2000.

(51) Int. Cl.[7] ............................ C01B 35/18; C07F 5/02; C09K 21/00; A01N 55/08
(52) U.S. Cl. ................ 252/601; 252/389.41; 423/277; 501/96.4; 514/64; 564/8
(58) Field of Search .......................... 252/601, 389.41; 423/277; 501/96.4; 514/64; 564/8

(56) References Cited

U.S. PATENT DOCUMENTS

| | | | |
|---|---|---|---|
| 3,116,326 A | 12/1963 | Glentworth | |
| 3,411,891 A | 11/1968 | Klanberg | |
| 4,002,681 A | 1/1977 | Goddard | |
| 4,130,585 A | * 12/1978 | Goddard | |
| 4,164,513 A | 8/1979 | Goddard | |
| 4,185,008 A | 1/1980 | Caspari et al. | |
| 4,202,712 A | 5/1980 | Goddard | |
| 4,265,664 A | 5/1981 | Saischek et al. | |
| 4,844,725 A | 7/1989 | Malouf et al. | |
| 5,061,698 A | 10/1991 | Malouf et al. | |
| 5,100,583 A | * 3/1992 | Malouf et al. | |
| 5,153,157 A | 10/1992 | Hlatky et al. | |
| 5,472,644 A | * 12/1995 | Schubert | 423/277 |
| 5,483,014 A | 1/1996 | Turner et al. | |
| 5,504,172 A | 4/1996 | Imuta et al. | |
| 5,581,010 A | 12/1996 | Cunningham et al. | |
| 5,616,663 A | 4/1997 | Imuta et al. | |
| 5,629,254 A | 5/1997 | Fukuoka et al. | |
| 5,658,997 A | 8/1997 | Fukuoka et al. | |
| 5,696,214 A | 12/1997 | Sagane et al. | |
| 5,698,651 A | 12/1997 | Kawasaki et al. | |
| 5,705,584 A | 1/1998 | Fukuoka et al. | |
| 5,710,223 A | 1/1998 | Fukuoka et al. | |
| 5,723,640 A | 3/1998 | Fukuoka et al. | |
| 5,739,366 A | 4/1998 | Imuta et al. | |
| 5,744,566 A | 4/1998 | Tsutsui et al. | |
| 5,753,769 A | 5/1998 | Ueda et al. | |
| 5,767,033 A | 6/1998 | Imuta et al. | |
| 5,807,948 A | 9/1998 | Sagane et al. | |
| 5,837,791 A | 11/1998 | Sagane et al. | |
| 5,840,808 A | 11/1998 | Sugimura et al. | |
| 5,854,354 A | 12/1998 | Ueda et al. | |
| 5,859,272 A | 1/1999 | Imuta et al. | |
| 5,922,823 A | 7/1999 | Sagane et al. | |
| 5,936,053 A | 8/1999 | Fukuoka et al. | |
| 5,959,046 A | 9/1999 | Imuta et al. | |
| 6,040,407 A | 3/2000 | Ishida et al. | |
| 6,133,490 A | 10/2000 | Toyoda et al. | |
| 6,136,743 A | 10/2000 | Sugimura et al. | |
| 6,143,264 A | * 11/2000 | Brattsev et al. | 423/283 |
| 6,177,526 B1 | 1/2001 | Fritze | |
| 6,194,501 B1 | 2/2001 | Okada et al. | |
| 6,235,818 B1 | 5/2001 | Morizono et al. | |
| 6,255,419 B1 | 7/2001 | Imuta et al. | |
| 6,271,164 B1 | 8/2001 | Fritze et al. | |
| 6,303,727 B1 | 10/2001 | Maeda et al. | |
| 6,313,243 B1 | 11/2001 | Tohi et al. | |
| 6,319,874 B1 | 11/2001 | Winter et al. | |
| 6,350,830 B1 | 2/2002 | Gores et al. | |
| 6,365,763 B1 | 4/2002 | Winter et al. | |
| 6,369,177 B1 | 4/2002 | Tohi et al. | |
| 6,403,719 B1 | 6/2002 | Tanaka et al. | |
| 6,433,130 B1 | 8/2002 | Shibayama et al. | |
| 6,444,606 B1 | 9/2002 | Bingel et al. | |
| 6,451,728 B1 | 9/2002 | Matsui et al. | |
| 6,458,982 B1 | 10/2002 | Schottek et al. | |
| 6,462,136 B1 | 10/2002 | Saito et al. | |
| 6,469,114 B1 | 10/2002 | Schottek et al. | |

(Continued)

FOREIGN PATENT DOCUMENTS

| | | |
|---|---|---|
| CA | 998325 A | 10/1976 |
| JP | 95102965 B2 | 1/1988 |
| JP | 63011505 A | 1/1989 |
| JP | 6-25343 A | 2/1994 |
| JP | 6041048 A | 2/1994 |

OTHER PUBLICATIONS

Rosenheim, A. and Leyser, F. "Polyborates in Aqueous Solution", (Thesis by F. Leyser, Berlin 1921), Z. Anorg. U. Allg. Chem., 119, 1–38, 1921, pp. 1–42, no month.

(Continued)

*Primary Examiner*—Wayne A. Langel
(74) *Attorney, Agent, or Firm*—Kurt R. Ganderup

(57) ABSTRACT

A family of borate compounds containing an isolated (finite) nonaborate anion with the structural formula $[B_9O_{12}(OH)_6]^{3-}$. Preferred amine nonaborate compounds have a resolved oxide formula of $A_2O \cdot 3B_2O_3 \cdot 2H_2O$, where A is the monovalent cation of an amine salt, such as guanidinium and imidazolium. Also provided is a method for preparing these compounds by crystallization from an aqueous solution under mild conditions without the formation of significant amounts of by-products. These compounds have potential application as precursors for the production of advanced boron nitride ceramic materials, and as flame retardants, corrosion inhibitors, and biocides.

27 Claims, No Drawings

U.S. PATENT DOCUMENTS

| | | |
|---|---|---|
| 6,486,277 B1 | 11/2002 | Erker et al. |
| 6,506,856 B2 | 1/2003 | Manders et al. |
| 6,583,237 B1 | 6/2003 | Imuta et al. |
| 6,583,238 B1 | 6/2003 | Göres et al. |
| 6,620,953 B1 | 9/2003 | Bingel et al. |
| 6,627,764 B1 | 9/2003 | Schottek et al. |
| 6,635,705 B2 | 10/2003 | Itoh et al. |
| 6,635,727 B1 | 10/2003 | Koda et al. |

OTHER PUBLICATIONS

Muetterties, E.L., "The Chemistry of Boron and its Compounds", John Wiley and Sons, Inc., 1967, pp. 177–181, no month.

Heller, G., "Die Hydrolyse von Borsauretrimethylester in Gegenwart Oftanischer Basen", J. Inorg. Nucl. Chem., Vol. 30, 1968, p. 2743–2754 (with partial translation), no month.

Christ, C.L. & Clark, J.R., "A Crystal–Chemical Classification of Borate Structures with Emphasis on Hydrated Borates", Phys. Chem. Minerals, 2, pp. 59–87 (1977), no month.

"Supplement to Mellor's Comprehensive Treatise on Inorganic and Theoretical Chemistry", Vol. V, Boron, Part A: Boron–Oxygen Compounds, Longman Group Ltd., 1980, pp. 694–702, no month.

Weakley, Timothy, "Guanidinium tetraborate(2–) Dihydrate", Acta Crystallographica, Sect. C. Cryst. Struct. Sommun. 1985, C41(3), pp. 377–379, no month.

Garrett, Donald E., "Borates Handbook of Deposits, Processing, Properties, and Use", Acad. Press, 1998, pp. 23–28, no month.

Burns, P.C. et al., "Borate Minerals. I. Polyhedral Clusters and Fundamental Building Blocks", in The Canadian Mineralogist, Vol. 33, Part 5, Oct. 1995, p. 1131–1151.

Grice, J.D. et al., "Borate Minerals. II. A Hierarchy of Structures Based on the Borate Fundamental Building Block", in The Canadian Mineralogist, 37, 1999, p. 731–762, no month.

Schubert at al., "Guanidinium and Imidazolium Borates containing the First Examples of an Isolated Nonaborate Oxo-anion: [B9O12(OH)6]3–", Inorganic Chemistry, Vol. 39, No. 11, Apr. 29, 2000, pp. 2250–2251.

Schubert et al., "First Examples of Isolated Nonaborate Oxo–anions: $[B_9O_{12}(OH)_6]^{3-}$", Abstract, American Chemical Society Division of Inorganic Chemistry. 219th ACS National Meeting, San Francisco, CA, Mar. 2000.

Grant B. Jacobsen et al., "Studies of 2,5;6,10;8,10–Tri–$\mu$–hydro–nonahydro–nido–nonaborate(1–), [B9H12]–: Preparation, Crystal and Molecular Structure, Nuclear Magnetic Resonance Spectra, Electrochemistry, and Reactions", J. Chem. Soc. Dalton Trans., 1985, pp 1645–1654, no month.

Dialog File 398: Chemsearch™ 1957–2003/Jun.; Search Bis and Tri and Butyl and Ammonium and Nonaborate.

Google Search: "nonaborate", dated Oct. 20, 2003.

Web page: http://www.boronchemist.com/B9ab.htm, Abstract, "Guanidinium and Imidazolium Borates Containing the First Examples of and Isolated Nonaborate Oxoanion: [B9O12(OH)6]3–". (Abstract for Cite No. 84), no date.

David M. Schubert et al., "Guanidinium and Imidazollum Borates Containing the First Examples of and Isolated Nonaborate Oxoanion: [B9O12(OH)6]3–", Inorg. Chem. 2000, 39, pp. 2250–2251. Published on Web Apr. 29, 2000.

Web page: http://www.boronchemist.com/Conferencetalks.htm, "Presentations at Conferences with Published Abstracts", no date.

Web page: http://www.boronchemist.com/publist.htm , "Publications—David M. Schubert, Ph. D.", no date.

Web page: http://www.znaturforsch.com/c55b.htm dated Oct. 20, 2003, Zeitschrift fur Naturforschung B, Contents vol. 55b (2000). Web–linked abstract #473 (attached) does not match title, no month.

Web page: http://www.chem.leeds.ac.uk/boronweb/jb.bould2.htm , Jonathan Bould Publications, no date.

Simon K. Boocock at al., "Some Ten–vertex niodo Metallaboranes; Oxidative insertion of Iridium(i) and Rhodium(I) Into the arachno–Nonaborate Anion, [B9H14]–, and the Crystal and Molecular Structure of 6–Hydride–66, bis(triphanylphosphine)–nido–6–tridadecaborane, [HIrB9H13][(PPh3)2]", J. Chem. Soc. Dalton Trans., 1982, pp. 713–719, no month.

Web page: http://www.chem.leeds.ac.uk/boronweb/6893pub.htm, Published Work 1968–1993 John D. Kennedy, no month.

Web page: http://www.ftir.cz/downloads/inorg2bo.txt, Nicodom spectral libraries, pp. 1–6, web page dated Oct. 20, 2003, publication date unknown.

Web page: http://www.malk.rssi.ru/contents/inrgchem; inrgchem11__1v46cont.htm , Contents Russian Journal of Inorganic Chemistry, vol. 46, No. 11, 2001, no month.

E.L Belokoneva et al., "New Nonlinear–Optical Pb3(OH)[B9O16][B(OH)3] Crystal with the Zeolite–Like Nonaborate Framework, Its Place in Systematization, and Structure–Genetic Relation to PbB4O7", Abstract, Russian Journal of Inorganic Chemistry, vol. 46, No. 11, 2001, no month.

Google cache, web page: http://216.239.53.104/search?q=cache:1OOJKA–JnuEJ:scilib.univ.kiev.ua/author.php%3F668+nonaborate&hl=en&ie=UTF–8, SciLib, pp. 1–8.

Web page: http://www.ezchem.pe.kr/chemworld/CW9609/name1.html, Copyright 1996, The Korean Chemical Society, no month.

Jelinek, Tomas et al., Chemical Abstracts, CA: 136(6)85855g, 2001, no month.

Gavrilova, L.A. et al., Chemical Abstracts, CA: 134(26)375387f, 2001, no month.

Jacobsen, Grant B. et al., Chemical Abstracts, CA: 103(26)226244q, 1985, no month.

Isaenko, L.I. et al., Chemical Abstracts, CA: 96(22)192358z, 1982, no month.

Toft, Mark A. et al., Chemical Abstracts, CA: 96(20)173360c, 1982, no month.

Leach. John B. et al., Chemical Abstracts, CA: 94(14)113665e, 1981, no month.

Kabbani, Raifah M. et al., Chemical Abstracts, CA: 90(4)33304p, 1978, no month.

Siedle, A.R. et al., Chemical Abstracts, CA: 81(8)44767g, 1974, no month.

Klanberg, Frank et al., Chemical Abstracts CA: 69(26)112991e, 1968, no month.

Klanberg, F. et al., Chemical Abstracts, CA: 69(10)40883w, 1968, no month.

Klanberg, Frank et al., Chemical Abstracts, CA: 67(8)39706t, 1967, no month.

Hertler, Walter R. et al., Chemical Abstracts, CA: 67(18)87350u, 1967, no month.

Drahota, Sdenek et al., Chemical Abstracts, CA:125:241567, 1966, no month.

Roth, Martin et al., Chemical Abstracts, CA: 124:202360, 1995, no month.

* cited by examiner

NONABORATE COMPOSITIONS AND THEIR PREPARATION

This Application is the National Stage of International Application No. PCT/US01/01711, filed Jan. 18, 2001, which claims the benefit under 35 U.S.C. 119(e) of U.S. Provisional Application No. 60/177,467, filed Jan. 21, 2000.

This invention relates to a family of borate compounds referred to as nonaborates and more particularly to the nonaborate compounds of guanidinium and imidazolium and methods for their preparation.

BACKGROUND OF THE INVENTION

Borate compounds (i.e. boron compounds in which boron is bonded only to oxygen) are useful in many industrial applications including the manufacture of glass and ceramics, fire retardancy, wood preservation and corrosion control. For fire retardant use, desirable attributes of borate compounds include ease of manufacture, a relatively high $B_2O_3$ content, and a high dehydration on-set temperature. The high dehydration temperature is important because it allows for processing in polymer systems at elevated temperatures. Borates are commonly used as flame retardant additives for polymers. For example zinc borate is often used as a partial substitute for antimony oxide in halogenated flame retard polymer compositions to reduce burn time times and/or afterglow in the standard UL-94 fire retardant test. Ceramics include both the common vitreous types and advanced ceramic materials.

Amine borate compositions are useful in a variety of applications including fertilizing plants (U.S. Pat. No. 4,844,725), inhibiting the corrosion of metals (U.S. Pat. No. 5,100,583), controlling insects and fungi, preserving wood (U.S. Pat. No. 5,061,698), and as boron nitride ceramic precursors (JP 95,102,965). In the case of borates used as precursors to advanced ceramics, important attributes include ease of preparation and an appropriate elemental ratio in the thermal decomposition products. The ability to produce such borate compounds under mild condition (at or near atmospheric pressure in aqueous media) greatly simplifies the manufacturing process, leading to better economics. Also, processes resulting in the production of little or no effluent are generally more economical and environmentally sound.

Borate compounds are typically ionic in character containing a boron oxoanion, such as the metaborate anion $[B(OH)_4]^-$, in combination with cationic species, such as sodium, $Na^+$. For example sodium metaborate is $Na^+$ $[B(OH)_4]^-$, also written as $Na_2B_2O_4 \cdot 4H_2O$ or as the resolved oxide formula, $Na_2O \cdot B_2O_3 \cdot 4H_2O$. Table 1 lists a number of well-known borate anions, including the structural formula and the resolved oxide formula for the corresponding compounds formed in combination with monovalent cations (represented by $M^+$).

TABLE 1

| Boron Oxoanion | Common Name | Structural Formula in Combination with Cation M+ | Resolved Oxide Formula |
|---|---|---|---|
| $[B(OH)_4]^-$ | metaborate | $M[B(OH)_4]$ | $M_2O \cdot B_2O_3 \cdot 4H_2O$ |
| $[B_4O_5(OH)_4]^{2-}$ | tetraborate | $M_2[B_4O_5(OH)_4]$ | $M_2O \cdot 2B_2O_3 \cdot 4H_2O$ |
| $[B_5O_6(OH)_4]^-$ | pentaborate | $M[B_5O_6(OH)_4]$ | $M_2O \cdot 5B_2O_3 \cdot 4H_2O$ |
| $[B_3O_3(OH)_4]^-$ | triborate | $M[B_3O_3(OH)_4]$ | $M_2O \cdot 3B_2O_3 \cdot 4H_2O$ |
| $[B_3O_3(OH)_5]^{2-}$ | triborate | $M_2[B_3O_3(OH)_5]$ | $2M_2O \cdot 3B_2O_3 \cdot 5H_2O$ |
| $[B_6O_7(OH)_6]^{2-}$ | hexaborate | $M_2[B_6O_7(OH)_6]$ | $M_2O \cdot 3B_2O_3 \cdot 3H_2O$ |

Structurally, each of these borate oxoanions has a different form. For example the metaborate anion has a tetrahedral form, while the tetraborate anion is a bridged eight-member B—O ring, the triborate anion is a six-member B—O ring (referred to as a boroxyl ring), the pentaborate anion consists of two six-member B—O rings sharing a common boron atom and the hexaborate anion consists of three B—O rings that share three boron atoms and one oxygen atom. Structural representations of several of these borate oxoanions are shown in Formulas I–V, below.

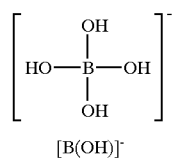

[B(OH)]⁻

Formula I

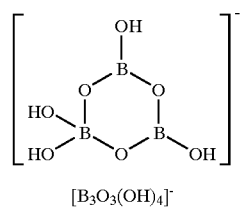

[B₃O₃(OH)₄]⁻

Formula II

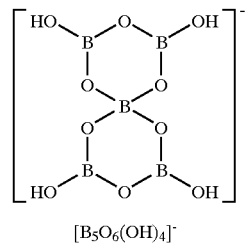

[B₅O₆(OH)₄]⁻

Formula I

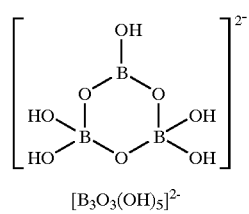

[B₃O₃(OH)₅]²⁻

Formula IV

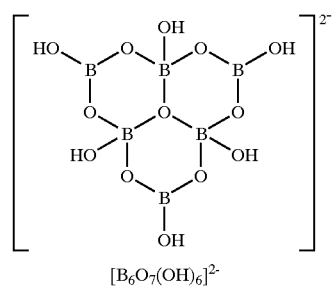

[B₆O₇(OH)₆]²⁻

Formula V

In the formation of natural minerals and synthetic borate compounds, these boron oxoanions are either isolated (finite), i.e. connected to adjacent boron oxoanions only by hydrogen bonds and not by oxygen bridges, or alternatively they are directly interconnected through boron-oxygen bonding into infinite chains, sheets or 3-dimensional framework structures. Borate minerals and synthetic compounds made up of isolated boron oxoanions containing from one to six boron atoms are quite common. Similarly, borate minerals and compounds containing infinite chains, sheets and 3-dimensional framework structures made up of repeating boron oxoanions (fundamental building blocks) having more than six boron atoms, such as the mineral preobrazhenskite, are also well known (Burns, P. C. et al., "Borate Minerals. I. Polyhedral Clusters and Fundamental Building Blocks", in *The Canadian Mineralogist,* 33, 1995, p. 1132–1133 and Grice, J. D. et al., "Borate Minerals. II. A Hierarchy of Structures Based on the Borate Fundamental Building Block", in *The Canadian Mineralogist,* 37, 1999, p. 731–762). However, isolated boron oxoanions having more than six boron atoms are rare and none have been reported with nine boron atoms.

Several amine borate compounds containing the guanidinium cation have been reported in the literature. Rosenheim and Leyser prepared guanidinium tetraborate (which they referred to as "biborate") by boiling guanidinium carbonate with the corresponding quantity of boric acid until no more carbon dioxide escaped, *Z. Anorg. U. Allg. Chem.,* 119, 1921, p. 1–38. They also prepared guanidinium tetraborate by precipitation in cold water by the treatment of concentrated borax solution with guanidinium chloride.

Heller described the preparation of a guanidinium pentaborate compound, formulated as $[C(NH_2)_3][B_5O_6(OH)_4]$, by the reaction of boric acid with guanidinium carbonate in boiling water, *J. Inorg. Nucl. Chem.,* Vol. 30, 1968, p. 2743–2754. Three crystalline guanidinium borate compounds containing free urea were prepared by hydrolysis of trialkoxyboron compounds with guanidine in ethanol and hydrocarbon solvent. These included $[C(NH_2)_3]_2[B_3O_3(OH)_5].(NH_2)_2C=O$, $[C(NH_2)_3]_3[B_4O_5(OH)_4].2(NH_2)_2C=O$, and $[C(NH_2)_3]_4[B_5O_6(OH)_7].(NH_2)_2C=O$.

G. H. Bowden, in "Supplement to Mellor's Comprehensive Treatise on Inorganic and Theoretical Chemistry", Vol. V, Boron, Part A: Boron-Oxygen Compounds, described two guanidinium borate compounds. The first is "guanidinium diborate" (i.e., tetraborate), $[(NH_2)_2=C=NH_2]_2O.2B_2O_3.4H_2O$, which is formed by reacting theoretical quantities of guanidinium carbonate and boric acid in a minimum of water at 90° C. Bowden also suggested that this compound may be produced from guanidinium chloride and borax. The second compound, guanidinium pentaborate hexahydrate, $[(NH_2)_2=C=NH_2]_2O.5B_2O_3.6H_2O$, was formed from guanidinium carbonate and the theoretical quantity of boric acid, in the same way as the diborate and can also be prepared from a mixture of borax and boric acid by treatment with guanidinium chloride. Bowden lists the pentaborate compound among several borate compounds investigated for possible use in citrus fruit preservation.

Ono Hiroshi described a method of producing boron nitride by heating a guanidine borate compound in inert or reductive atmosphere at 600° C. or higher in, "Manufacturing Method of Boron Nitride", JP 95,102,965 (JP 63,011,505), 1995, Mitsu Toatsu Chemicals, Inc. The guanidine borate compounds proposed for use are of the composition $x[C(NH_2)_3]_2O.yB_2O_3.zH_2O$ (where x and y can be 1–5 and z can be 0–9), which are prepared by the reaction of free guanidine with boric acid or boric oxide in water in the appropriate ratios. Free guanidine was prepared by passing a solution of guanidine carbonate through a column of strongly basic ionic exchange resin to remove the carbonate radical. Hiroshi further suggests that guanidine can be replaced by substituted guanidine $(R^1R^2NC(=NH)NR^3R^4$, where $R^{1-4}=H$, alkyl, aryl, cyanoalkyl, or hydroxyalkyl, and $R^1$ may be an amino group).

Tetsuo Yoshiyama described the preparation of guanidinium borate compounds by reaction of guanidine and a variety of substituted guanidine compounds $(R^1R^2NC(=NH)NR^3R^4$, where $R^{1-4}=H$, alkyl, aryl, or hydroxyalkyl, and $R^1$ may be an amino group) with alkoxyboron compounds in organic solvent and water (see "Manufacturing Method of Borate of Guanidine Compound", JP 94,041,048 (JP 06,041,048), 1994, Mitsu Toatsu Chemicals, Inc. The product obtained using unsubstituted guanidine was a non-crystalline, alkaline, solid powder having the chemical composition 10.8% C, 7.0% H, 32.8% N, and 9.3% B. This composition is similar to $[C(NH_2)_3]_2[B_3O_3(OH)_5].(NH_2)_2C=O$ produced by Heller.

Applicant has unexpectedly found a family of borate compounds containing an isolated nonaborate oxoanion which is the first reported example of an isolated nonaborate anion in a hydrated borate (the term "hydrated borate" refers to borate compounds that possess B—OH groups, which may or may not also contain free water of crystallization.)

BRIEF DESCRIPTION OF THE INVENTION

The present invention relates to a family of novel borate compounds containing an isolated nonaborate anion, $[B_9O_{12}(OH)_6]^{3-}$. Amine borates of this family have a resolved oxide formula of $A_2O.3B_2O_3.2H_2O$, where A is a cationic amine, such as guanidinium or imidazolium. This invention also provides a method for preparing these compounds by crystallization from an aqueous solution under mild conditions without the formation of significant amounts of by-products. This invention further provides a method for the use of these novel nonaborate compounds in the formation of boron nitride precursors to advanced boron nitride ceramic materials.

DETAILED DESCRIPTION OF THE INVENTION

The present invention relates to a new family of borate compounds containing an isolated nonaborate oxoanion, $[B_9O_{12}(OH)_6]^{3-}$. The chemical structure of the nonaborate oxoanion is shown in Formula VI, below.

Formula VI

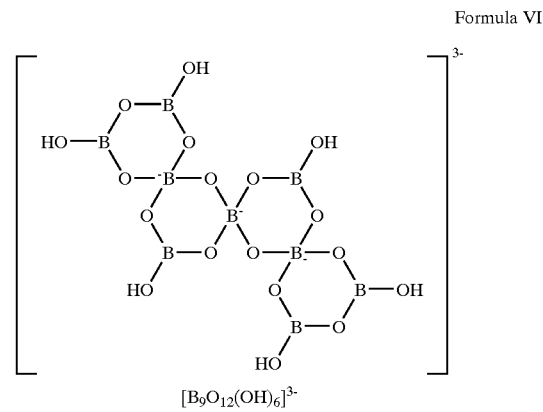

$[B_9O_{12}(OH)_6]^{3-}$

The nonaborate oxoanion combines with three monovalent cations, such as guanidinium or imidizolium, to form the preferred compounds of this invention. Structurally, the nonaborate oxoanion consists of four fused boroxyl rings $(B_3O_3)$ joined by three shared boron atoms. The outer two boroxyl rings each have one shared and two non-shared boron atoms, with a terminal —OH group on each of the non-shared boron atoms. The two inner boroxyl rings each have two shared and one non-shared boron atom, with a terminal —OH group on each of the non-shared boron atoms. Overall this oxoanion contains three tetrahedral boron centers, shared between the rings, and six trigonal non-shared boron centers, in contrast to the four boroxyl rings of the mineral preobrazhenskite which contain a total of five tetrahedral and four trigonal boron centers. The nonaborate compounds of this invention are sometimes referred to as "hydrated borates" due to the presence of B—OH groups, but do not necessarily also contain free water of crystallization.

The preferred compounds of this invention have the chemical formula $A_3[B_9O_{12}(OH)_6]$, where A is a monovalent cation, such as guanidinium or imidazolium. Such compounds have a resolved oxide formula of $A_2O_3 \cdot B_2O_3 \cdot 2H_2O$.

One preferred embodiment of this invention is guanidinium nonaborate, a compound having the structural formula $[C(NH_2)_3]_3[B_9O_{12}(OH)_6]$ and a resolved oxide formula of $[C(NH_2)_3]_2O \cdot 3B_2O_3 \cdot 2H_2O$. Guanidinium nonaborate is a white microcrystalline powder with a $B_2O_3$ content greater than 54% and a dehydration on-set temperature above 200° C. In this compound, the nonaborate oxoanion is associated with three guanidinium cations that exhibit extensive hydrogen bonding interactions with the borate anion. There is no free water in the crystal, which accounts for the unusually high dehydration temperature of this compound. Guanidinium nonaborate can be prepared in aqueous solution under atmospheric pressure at or below the boiling point without the formation of significant amounts of by-products. Alternatively, if desired, it can be prepared at elevated pressures and temperatures above 100° C. It has a theoretical composition 54.8% $B_2O_3$, 35.7% $[C(NH_2)_3]_2O$ and 9.5% $H_2O$. The dehydration on-set temperature of this substance is high enough to allow processing in a wide variety of polymer materials. Furthermore, this compound has potential application as a ceramic precursor that may provide a convenient route to a form of boron nitride upon pyrolysis. It is also potentially useful in fungicidal and related applications.

Guanidinium nonaborate may be prepared by the reaction of borax and boric acid with guanidinium salts at elevated temperature in aqueous media. Sources of guanidinium include such salts as guanidinium carbonate, $[C(NH_2)_3]_2CO_3$, (also known as guanidine carbonate), guanidinium chloride, $[C(NH_2)_3]Cl$, (also known as guanidine chloride), guanidinium thiosulfate, and guanidinium sulfate.

In order to obtain the desired nonaborate compound, as opposed other previously known guanidinium borates, the reaction must be carried out under specific conditions of temperature and chemical concentrations. The formation of guanidinium nonaborate from guanidinium carbonate and boric acid is believed to result from the following reaction:

$$[C(NH_2)_3]_2CO_3 + 6B(OH)_3 \rightarrow$$
$$[C(NH_2)_3]_2O \cdot 3B_2O_3 \cdot 2H_2O + CO_2 + 7H_2O \qquad \text{Eq. 1}$$

The ratio of reactants is a critical requirement in obtaining guanidinium nonaborate as opposed to other, previously known, guanidinium borates. The $B_2O_3/[C(NH_2)_3]_2O$ ratio of the reaction mixture is referred to as the q value, whereas the $B_2O_3/[C(NH_2)_3]_2O$ of the product solids is referred to as the Q value. Guanidinium nonaborate forms readily at q values from about 2.5 to about 4–5, in reactions carried out with guanidinium carbonate and boric acid at 90° C. At a q value of 2 or lower, guanidinium tetraborate, $[C(NH_2)_3]_2O \cdot 2B_2O_3 \cdot 4H_2O$, is obtained. At a q value of about 5 the resultant product may be guanidinium nonaborate or a nonaborate/pentaborate mixture or boric acid alone, depending on the overall concentration of the reactants.

At q=3 (the exact stoichiometry for guanidinium nonaborate), varying the overall concentration over a wide range has no effect on the formation of guanidinium nonaborate, but does effect yield. Higher yields are obtained at higher concentrations. At a q value of 3.0, guanidinium nonaborate is obtained at temperatures above about 45° C. The nonaborate is formed at temperatures up to and even above the boiling point of the solution, such as at 120° C., and elevated pressure conditions. At a temperature of 45° C. and below, guanidinium tetraborate is obtained.

Guanidinium nonaborate can also be prepared by the reaction of guanidinium salts with borate salts, such as by the reaction of guanidinium chloride with a mixture of borax and boric acid in hot aqueous solution according to the following reaction (Eq. 2).

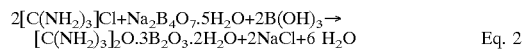
$$2[C(NH_2)_3]Cl + Na_2B_4O_7 \cdot 5H_2O + 2B(OH)_3 \rightarrow$$
$$[C(NH_2)_3]_2O \cdot 3B_2O_3 \cdot 2H_2O + 2NaCl + 6 H_2O \qquad \text{Eq. 2}$$

Alternatively, guanidinium nonaborate can be prepared by the reaction of guanidinium tetraborate dihydrate with boric acid.

Another preferred embodiment of this invention is imidazolium nonaborate, which has the structural formula $[C_3H_5N_2]_3[B_9O_{12}(OH)_6]$ and a resolved oxide formula $[C_3H_5N_2]_2O \cdot 3B_2O_3 \cdot 2H_2O$. Imidazolium nonaborate can be prepared by crystallization from an aqueous stoichiometric mixture of boric acid and imidazole (Eq. 3). Imidazolium nonaborate forms at temperatures from room temperature up to at least 100° C., although at room temperature the product can be difficult to handle due to its relatively low solubility in water.

Eq. 3

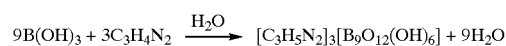
$$9B(OH)_3 + 3C_3H_4N_2 \xrightarrow{H_2O} [C_3H_5N_2]_3[B_9O_{12}(OH)_6] + 9H_2O$$

It is notable that the guanidine-borate and imidazole-borate systems contrast with the ammonium-borate system, which has been studied extensively. Whereas ammonium tetraborate and pentaborate are well known, ammonium nonaborates not produced at intermediate q values.

The compositions of this invention have potential application as precursors for advanced boron nitride ceramics. For example, guanidinium nonaborate has a B:N mole ratio of 1.0, suggesting that it might be useful in this application. Guanidinium nonaborate does not melt below 1000° C., but instead decomposes upon heating to a refractory material. It begins to lose weight when heated above about 220° C. Initial weight loss is primarily due to elimination of water by condensation of B—OH groups. Upon further heating some ammonia and carbon dioxide is lost resulting in a ceramic-like material having a mole ratio of B:N>1. Imidazolium nonaborate exhibits similar decomposition behavior, with elimination of water commencing at about 180° C. Equation 4 expresses the proposed reaction for conversion of guanidinium nonaborate to boron nitride. Theoretical yield of boron nitride for this reaction is 48.8%. Imidazolium nonaborate exhibits a similar thermal decomposition behavior.

Eq. 4

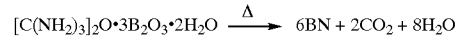
$$[C(NH_2)_3]_2O \cdot 3B_2O_3 \cdot 2H_2O \xrightarrow{\Delta} 6BN + 2CO_2 + 8H_2O$$

EXAMPLES

Example 1

Synthesis and Characterization of Guanidinium Nonaborate

A 1-liter flask was fitted with a reflux condenser, 1.0L heating mantle, magnetic stirrer, and temperature controller.

The flask was charged with 225 mL deionized water and 360.3 g (2.0 moles) guanidinium carbonate. The resulting solution was heated to about 45° C. and 742.0 g (12.0 moles) boric acid was added with stirring. The mixture was then heated to 90° C. and maintained at this temperature with stirring. Evolution of carbon dioxide was noted immediately after boric acid addition and during the initial stages of heating. After maintaining the mixture at 90° C. for one hour with stirring, the resulting slurry was cooled to about 60° C. and filtered to isolate the solid product (Compound I). The final pH of the mixture was about 8.1. The solid product was washed with about 200 mL deionized water and dried in air at 40° C.

Compound I was a white microcrystalline powder. It was subjected to x-ray diffraction and thermogravimetric analysis in addition to elemental analysis. The results of the chemical analyses, given in Table 2, below, correspond to a composition of $[C(NH_2)_3]_2O.3B_2O_3.2H_2O$.

TABLE 2

Elemental Analysis of Compound I

| Analyzed for | Measured Composition | Calculated for $[C(NH_2)_3]_2O.3B_2O_3.2H_2O$ |
| --- | --- | --- |
| Carbon | 6.25% | 6.30% |
| Hydrogen | 4.33 | 4.27 |
| Nitrogen | 21.46 | 22.06 |
| Boron | 17.32 | 17.02 |
| Oxygen (by difference) | 50.64 | 50.39 |

X-ray diffraction analysis of Compound I showed that the crystalline solid does not contain free water. Thermogravimetric analysis at a scanning rate of 1° C./min indicated a dehydration on-set temperature of about 200° C. This unusually high dehydration temperature is consistent with the lack of free water in the crystal structure. Compound I was found to be stable in aqueous solution in the presence of excess boric acid, but decomposed when stirred for prolonged periods of time in pure water. Recrystallization from water resulted in quantitative conversion to guanidinium tetraborate tetrahydrate and boric acid.

Example 2

Single-Crystal X-Ray Structure of Compound I

In order to obtain crystals sufficiently large in size to allow detailed x-ray crystallography analysis, the preparation of Compound I was repeated according to the procedure of Example 1, except that the mixture was maintained at 90° C. for ten days, instead of being filtering after one hour. Powder x-ray diffraction and titration analyses indicated that the product obtained was the same as that from Example 1. The product was screened to isolate a fraction containing some coarse crystals. From this coarse fraction, one single crystal was selected, mounted on a glass fiber using epoxy cement, and used to collect x-ray diffraction data for crystallography studies.

Analysis of the x-ray data revealed a structure containing a single borate oxoanion accompanied by three guanidinium cations. The borate oxoanion, of composition $[B_9O_{12}(OH)_6]^{3-}$, is shown schematically in Formula VI. This anion consists of four fused boroxyl ($B_3O_3$) rings joined by three shared boron atoms. The two inner boroxyl rings each possess one terminal —OH group on the non-shared boron atom, whereas the outer two rings each have two terminal —OH groups on the two non-shared boron atoms. This oxoanion contains three tetrahedral boron centers, shared between the rings, and six trigonal boron centers. This nonaborate anion is associated with three guanidinium cations that exhibit extensive hydrogen bonding interactions with polyborate anion. There is no free water in the crystal. These results are consistent with the formulation for Compound I determined by chemical analysis in Example 1, i.e. the resolved oxide formulation $[C(NH_2)_3]_2O.3B_2O_3.2H_2O$ is equivalent to the observed structural formula $[C(NH_2)_3]_3[B_9O_{12}(OH)_6]$. This compound is referred to as guanidinium nonaborate.

Example 3

Crystallization Fields for the $B_2O_3$—$[C(NH_2)_3]_2O$ System at 90° C.

A series of experiments was carried out in which guanidinium carbonate and boric acid were reacted at 90° C. The reaction method was the same as in Example 1, except the reactant amounts were varied to give $B_2O_3:[C(NH_2)_3]_2O$ mole ratios ranging from 0.5:1 to 5.0:1. The $B_2O_3/[C(NH_2)_3]_2O$ ratio of the reaction mixture is referred to as the q value, whereas the $B_2O_3/[C(NH_2)_3]_2O$ of the product solids is referred to as the Q value. The results of these experiments are shown in Table 3.

TABLE 3

Summary of Results from Guanidinium Carbonate-Boric Acid Reactions Run at 90° C.

| Experiment | $[B_2O_3]_{initial}$[1] | $[G_2O]_{initial}$[2] | q[3] | Q[4] | Product Obtained |
| --- | --- | --- | --- | --- | --- |
| 1 | 0.56 | 1.11 | 0.5 | 2.0 | Guanidinium Tetraborate |
| 2 | 0.56 | 0.56 | 1.0 | 2.0 | Guanidinium Tetraborate |
| 3 | 1.11 | 1.11 | 1.0 | 2.0 | Guanidinium Tetraborate |
| 4 | 1.67 | 1.11 | 1.5 | 2.0 | Guanidinium Tetraborate |
| 5 | 1.11 | 0.56 | 2.0 | 2.0 | Guanidinium Tetraborate |
| 6 | 2.22 | 1.11 | 2.0 | 2.0 | Guanidinium Tetraborate |
| 7 | 2.78 | 1.11 | 2.5 | 3.0 | Guanidinium Nonaborate |
| 8 | 1.67 | 0.56 | 3.0 | 3.0 | Guanidinium Nonaborate |
| 9 | 0.56 | 2.46 | 3.0 | 3.0 | Guanidinium Nonaborate |
| 10 | 3.33 | 1.11 | 3.0 | 3.0 | Guanidinium Nonaborate |
| 11 | 4.44 | 1.48 | 3.0 | 3.0 | Guanidinium Nonaborate |
| 12 | 6.67 | 2.22 | 3.0 | 3.0 | Guanidinium Nonaborate |
| 13 | 3.89 | 1.11 | 3.5 | 3.0 | Guanidinium Nonaborate |

TABLE 3-continued

Summary of Results from Guanidinium Carbonate-Boric Acid Reactions Run at 90° C.

| Experiment | $[B_2O_3]_{initial}$[1] | $[G_2O]_{initial}$[2] | q[3] | Q[4] | Product Obtained |
|---|---|---|---|---|---|
| 14 | 2.22 | 0.56 | 4.0 | 3.0 | Guanidinium Nonaborate |
| 15 | 4.45 | 1.11 | 4.0 | 3.0 | Guanidinium Nonaborate |
| 16 | 2.77 | 0.56 | 5.0 | 3.0 | Guanidinium Nonaborate |
| 17 | 4.10 | 0.82 | 5.0 | 3.0 and 5.0 | Guanidinium Nonaborate and Guanidinium Pentaborate |
| 18 | 5.55 | 1.11 | 5.0 | — | Boric Acid |
| 19 | 0.22 | 0.04 | 6.0 | — | Nothing crystallized |
| 20 | 3.33 | 0.56 | 6.0 | 5.0 | Guanidinium Pentaborate |

[1] $[B_2O_3]_{initial}$ is the equivalent initial $B_2O_3$ molar concentration (moles per liter) supplied by boric acid reagent.
[2] $[G_2O]_{initial}$ is the equivalent initial $[(C(NH_2)_3)_2O$ molar concentration (moles per liter) supplied by guanidinium carbonate reagent.
[3] q is $[B_2O_3]_{initial}/[G_2O]_{initial}$ ratio.
[4] Q is $[B_2O_3]_{product}/[G_2O]_{product}$ ratio.

Guanidinium nonaborate was obtained only at q values greater than 2. Guanidinium nonaborate formed readily at q values between about 2.5 and 4. At q=2 or less, only the tetraborate was obtained. At q=3 (exact stoichiometry for guanidinium nonaborate), varying concentration over a wide range had no effect on the formation of guanidinium nonaborate, but did effect yield. At q=4, guanidinium nonaborate was again consistently obtained. At q=5, the composition of the reaction product was dependent on the overall concentration of the reaction mixture. At lower concentrations, guanidinium nonaborate was obtained. As the concentration of reactants increased at q=5, the product composition changed, first to a mixture of guanidinium nonaborate plus guanidinium pentaborate, and then, as the concentration increased further, a product consisting essentially of pure boric acid was obtained. At q values greater than 5 and relatively lower overall concentrations the pentaborate was obtained. In general, higher yields were obtained at higher concentrations, but the slurry became too viscous to be easily managed in the highest concentration experiment.

Example 4

Effect of Temperature on the Formation of Guanidinium Nonaborate

A series of experiments was conducted according to the procedure described in Example 1 in which the reaction mixtures were maintained for approximately one hour at temperatures of 20, 45, 50, 60, 70, 90, and 100° C. An additional experiment was carried out by placing a flask containing the starting reagents and water in an autoclave at 120° C. for one hour. The results of these experiments indicate that at a q value of 3.0 compound guanidinium nonaborate is only obtained at temperatures above about 45° C. Below this temperature, the tetraborate product (Q=2) is found, even though the reaction mixture has a q value of 3. The results are summarized in Table 4.

TABLE 4

Effect Of Temperature At Q = 3.0

| Temperature (° C.) | Q | Product |
|---|---|---|
| 20 | 2.0 | Guanidinium Tetraborate |
| 45 | 2.0 | Guanidinium Tetraborate |
| 50 | 3.0 | Guanidinium Nonaborate |
| 60 | 3.0 | Guanidinium Nonaborate |
| 70 | 3.0 | Guanidinium Nonaborate |
| 90 | 3.0 | Guanidinium Nonaborate |
| 120 | 3.0 | Guanidinium Nonaborate |

Example 5

Preparation from Guanidinium Chloride, Borax and Boric Acid

A 1-liter flask was fitted with a reflux condenser, heating mantle, magnetic stirrer, and temperature controller. The flask was charged with 225 mL deionized water and 47.77 g (0.50 moles) guanidinium chloride. The resulting solution was heated to about 40° C. and 72.84 g (0.25 moles) sodium tetraborate pentahydrate was added with stirring. The mixture was then heated to 90° C. and maintained with stirring. After maintaining one hour the resulting slurry was cooled to about 50° C. and filtered. The final pH of the mixture was 8.2. The resulting white solid was washed with about 200 mL deionized water and dried in air at 40° C. The product was identified by x-ray diffraction, thermogravimetric analysis, and titration analysis as substantially pure guanidinium nonaborate.

Example 6

Preparation from Boric Acid and Guanidinium Tetraborate

A flask fitted with a reflux condenser, magnetic stirrer, and temperature controller was charged with 225 mL deionized water and 86.9 g (0.25 moles) guanidinium tetraborate dihydrate. After heating to about 45° C., 30.9 g (0.50 moles) boric acid was added with stirring. The mixture was then heated to 90° C. and maintained with stirring for 1 hour. The slurry was then cooled to about 45° C. and filtered. The resulting white solid was washed with about 100 mL deionized water and dried at 105° C. It was identified as guanidinium nonaborate by x-ray diffraction and titration analysis.

Example 7

Preparation of Imidazolium Nonaborate

A flask fitted with a reflux condenser, magnetic stirrer, and temperature controller was charged with 225 mL deionized water and 70.0 g (1.0 moles) imidazole ($C_3H_4N_2$). The resulting solution was heated to about 45° C. and 185.5 (3.0 moles) boric acid was added with stirring. The mixture was then heated to 90° C. and maintained with stirring for 1 h, cooled to 45° C., filtered, and washed with water. The resulting white powder was washed with about 100 mL deionized water and dried at 105° C. It was identified as imidazolium nonaborate by x-ray diffraction and titration analysis. Elemental analyses for the product are shown in Table 5, along with the theoretical analyses for imidazolium nonaborate, $[C_3H_5N_2]_2O.3B_2O_3.2H_2O$.

TABLE 5

Imidazolium Nonaborate Product Analyses

| | Analysis | |
|---|---|---|
| Component | Theoretical | Measured |
| Carbon, % | 18.06 | 18.13 |
| Hydrogen, % | 3.53 | 3.49 |
| Nitrogen, % | 14.04 | 14.12 |
| Boron, % | 16.25 | 16.67 |

Example 8

Conversion of Guanidinium Nonaborate to a Ceramic Material by Pyrolysis

A 10.00 g sample of guanidinium nonaborate was placed into a Lindberg Box Furnace. The furnace was purged with $N_2$ gas at room temperature for about one hour and then heated to 850° C. The sample was held at 850° C. for about 2.5 hours and then cooled to room temperature with a continuous $N_2$ purge. The resulting material was a consolidated white powder that was easily crushed to a free-flowing powder. The sample lost 5.13 g during the pyrolysis, to give a product yield of 48.70%. This is consistent with Equation 4.

X-ray diffraction analysis of the pyrolysis product indicated that it was largely amorphous, but contained some structures suggestive of hexagonal boron nitride. Element analysis of the pyrolysis product yielded the following composition: 31.93% B, 16.96 and 17.14% N (two determinations), and 50.94% O (by difference). No carbon or hydrogen was found (i.e., <0.5%). This analysis indicates that the pyrolysis product had the composition: $B_{1.43-1.45}N_{1.00}O_{3.36-3.44}$.

Example 9

Use of Guanidinium Nonaborate as a Flame Retardant

A series of experiments was run to evaluate the effect of guanidinium nonaborate on afterglow time when used as a partial substitute for antimony oxide as a flame retardant in a bromine-containing polypropylene resin system. Composition A was prepared by compounding polypropylene resin (commercially available from Montell, a subsidiary of the Royal Dutch/Shell Group, as Montell 6523) was compounded with a polypropylene coupling agent (commercially available from Uniroyal Chemical Company, Inc. as Polybond 3150), talc, DBDPO (decabromodiphenyloxide), a common halogen source used in polymer compositions) and antimony oxide ($Sb_2O_3$). Compositions B, C and D had essentially the same composition as composition A, except for replacement of 25, 50, and 75% of the antimony oxide, respectively, with guanidinium nonaborate (Compound I). The compositions of A, B, C and D are described in Table 6. The afterglow times for compositions A, B, C and D were evaluated according to the standard UL-94 test. The test results are shown in Table 6.

TABLE 6

Flame Retardant Composition Containing Guanidinium Nonaborate

| | Percent Composition (w/w) | | | |
|---|---|---|---|---|
| | A | B | C | D |
| COMPONENT | | | | |
| Montell 6523 | 51.9 | 51.9 | 51.9 | 51.9 |
| Polybond 3150 | 1.0 | 1.1 | 1.1 | 1.1 |
| Talc | 19.8 | 20.0 | 20.0 | 20.0 |
| DBDPO | 17.9 | 17.0 | 17.0 | 17.0 |
| Antimony oxide | 10.0 | 7.5 | 5.0 | 2.5 |
| Guanidinium nonaborate | 0.0 | 2.5 | 5.0 | 7.5 |
| Test Results | | | | |
| UL-94 Rating (⅛ inch) | V-0 | V-0 | V-0 | V-0 |
| Total Afterglow Time | 40.8 | 11.0 sec | 7.5 sec | 2.2 sec |

A V-0 rating in the UL-94 test indicates that the sum of the burn times (including afterglow) for five samples, with two 10 second ignitions each using a standard flame, was less than 50 seconds and no individual sample burned longer than 10 seconds. V-0 also indicates that no sample produced burning drips that ignited a piece of cotton positioned beneath the sample.

A reduction in afterglow time was obtained with maintenance of a V-0 (passing) rating at all levels of substitution with guanidinium nonaborate. Compositions containing mixtures of antimony oxide and the nonaborate (compositions B, C and D) provided significantly better afterglow performance than the composition containing antimony oxide without the borate, even at a higher level of bromine.

Various changes and modifications of the invention can be made and, to the extent that such variations incorporate the spirit of this invention, they are intended to be included within the scope of the appended claims.

What is claimed is:

1. A crystalline nonaborate compound comprising an isolated nonaborate anion having the formula $[B_9O_{12}(OH)_6]^{3-}$.

2. The compound according to claim 1 wherein said anion has the chemical structure

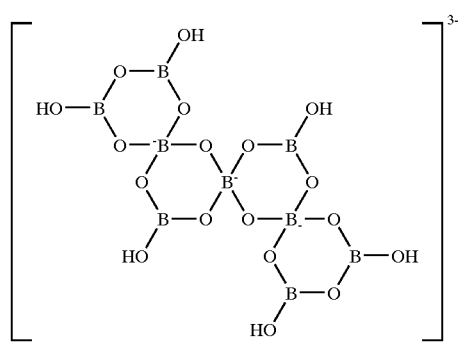

3. The compound according to claim 2 having a chemical formula of $A_3[B_9O_{12}(OH)_6]$, wherein A is a monovalent cation.

4. The compound according to claim 3 wherein A is a monovalent cationic amine.

5. The compound according to claim 4 wherein A is guanidinium.

6. A method for producing the crystalline nonaborate compound of claim 5 comprising reacting boric acid with a guanidinium salt in hot aqueous media wherein the molar ratio of $B_2O_3:[C(NH_2)_3]_2O$ in said reaction is in the range of from about 2.5:1 to about 5:1.

7. The method according to claim 6 wherein said reaction is carried out at a temperature above 45° C.

8. The method according to claim 7 wherein said temperature is in the range of about 50° C. to 120° C.

9. The method according to claim 8 wherein said guanidinium salt is selected from the group consisting of guanidinium carbonate, guanidinium chloride, guanidinium thiosulfate, and guanidinium sulfate.

10. The method according to claim 8 wherein said guanidinium salt is guanidinium carbonate.

11. The method according to claim 8 wherein the molar ratio of $B_2O_3:[C(NH_2)_3]_2O$ in said reaction is in the range of from about 2.5:1 to about 4:1.

12. The method according to claim 8 wherein the molar ratio of $B_2O_3:[C(NH_2)_3]_2O$ in said reaction is about 3:1.

13. A method for producing the crystalline nonaborate compound of claim 5 comprising reacting a guanidinium salt with borate salts in hot aqueous media wherein the molar ratio of $B_2O_3:[C(NH_2)_3]_2O$ in said reaction is in the range of from about 2.5:1 to about 5:1.

14. The method according to claim 13 wherein said guanidinium salt is guanidinium chloride.

15. The method according to claim 13 wherein said borate salts comprise boric acid and sodium borate.

16. The method according to claim 15 wherein guanidinium chloride is reacted with a mixture of boric acid and sodium tetraborate pentahydrate.

17. A method for producing the crystalline nonaborate compound of claim 5 comprising reacting guanidinium tetraborate dihydrate with boric acid in hot aqueous media wherein the molar ratio of $B_2O_3:[C(NH_2)_3]_2O$ in said reaction is in the range of from about 2.5:1 to about 5:1.

18. The compound according to claim 4 wherein A is imidazolium.

19. A method for producing the crystalline nonaborate compound of claim 18 comprising reacting boric acid with imidazole in aqueous media.

20. The method according to claim 19 wherein said reaction is carried out at a temperature in the range of about 20° C. to 100° C.

21. A method of preparing a boron nitride ceramic precursor comprising heating the compound of claim 4 at a temperature in the range of about 650° C. to 1200° C.

22. The method according to claim 21 wherein said compound is selected from the group consisting of guanidinium nonaborate and imidazolium nonaborate.

23. A boron nitride ceramic precursor composition prepared according to the method of claim 22.

24. A fire retardant composition comprising an effective amount of the crystalline nonaborate compound of claim 4.

25. A fire retardant composition comprising talc-filled polypropylene with a bromine source, antimony oxide, and an effective amount of the crystalline nonaborate compound of claim 4.

26. A biocidal composition comprising an effective amount of the crystalline borate compound of claim 4.

27. A corrosion inhibiting composition comprising an effective amount of the crystalline borate compound of claim 4.

* * * * *